(12) United States Patent
Foucher et al.

(10) Patent No.: US 9,993,597 B2
(45) Date of Patent: Jun. 12, 2018

(54) LUBRICANT COATING AND MEDICAL INJECTION DEVICE COMPRISING SUCH A COATING

(71) Applicant: Becton Dickinson France, Le Pont de Claix (FR)

(72) Inventors: Cédric Foucher, Grenoble (FR); Virginie Santucci-Aribert, Moirans (FR)

(73) Assignee: Becton Dickinson France, Le Point de Claix (FR)

( * ) Notice: Subject to any disclaimer, the term of this patent is extended or adjusted under 35 U.S.C. 154(b) by 668 days.

(21) Appl. No.: 14/404,153

(22) PCT Filed: May 29, 2013

(86) PCT No.: PCT/EP2013/061007
§ 371 (c)(1),
(2) Date: Nov. 26, 2014

(87) PCT Pub. No.: WO2013/178647
PCT Pub. Date: Dec. 5, 2013

(65) Prior Publication Data
US 2015/0165125 A1    Jun. 18, 2015

(30) Foreign Application Priority Data
May 29, 2012    (EP) .................................... 12305592

(51) Int. Cl.
*B01D 19/04*    (2006.01)
*A61M 25/00*    (2006.01)
(Continued)

(52) U.S. Cl.
CPC ........... *A61M 5/3129* (2013.01); *B05D 3/147* (2013.01); *B05D 3/148* (2013.01); *C10M 107/50* (2013.01);
(Continued)

(58) Field of Classification Search
CPC . C10M 2227/02; A61L 31/10; A61M 5/31513
See application file for complete search history.

(56) References Cited

U.S. PATENT DOCUMENTS 3,847,652 A    11/1974 Fletcher et al.
4,767,414 A    8/1988 Williams et al.
(Continued)

FOREIGN PATENT DOCUMENTS

EP    0201915 A2    11/1986
EP    0920879 A2    6/1999
(Continued)

OTHER PUBLICATIONS

Carpenter et al.; "Overlooking Subvisible Particles in Therapeutic Protein Products: Gaps that may Compromise Product Quality"; J. Pharm Sci.; Apr. 2009; pp. 1201-1205; 98(4); doi: 10.1002/jps. 21530.
(Continued)

*Primary Examiner* — Vishal Vasisth
(74) *Attorney, Agent, or Firm* — The Webb Law Firm

(57) ABSTRACT

The invention relates to a lubricant coating (5) for a medical injection device (1), comprising successively: —a bottom layer (50) in contact with the medical device surface (21) of the container to be lubricated, comprising a mixture of cross-linked and non-cross-linked poly-(dimethylsiloxane), —an intermediate layer (51) consisting essentially of oxidized poly-(dimethylsiloxane) and having a thickness comprised between 10 and 30 nm and, —a top layer (52) consisting essentially of non-cross-linked poly-(dimethylsiloxane) and having a thickness of at most 2 nm. The invention also relates to a medical injection device comprising such a lubricant coating, and a manufacturing process for said coating.

11 Claims, 8 Drawing Sheets

(51) Int. Cl.
    *B05D 3/00*            (2006.01)
    *A61M 5/315*         (2006.01)
    *A61M 5/31*          (2006.01)
    *C10M 107/50*       (2006.01)
    *B05D 3/14*          (2006.01)
    *C10M 155/02*       (2006.01)

(52) U.S. Cl.
    CPC ... C10M 155/02 (2013.01); *A61M 2005/3131* (2013.01); *A61M 2205/0222* (2013.01); *A61M 2205/0238* (2013.01); *C10M 2229/0415* (2013.01); *C10N 2240/66* (2013.01); *C10N 2250/14* (2013.01); *C10N 2260/04* (2013.01); *C10N 2270/00* (2013.01)

(56) References Cited

U.S. PATENT DOCUMENTS

| | | | |
|---|---|---|---|
| 4,822,632 A | 4/1989 | Williams et al. | |
| 5,338,312 A | 8/1994 | Montgomery | |
| 6,461,334 B1 | 10/2002 | Buch-Rasmussen et al. | |
| 7,553,529 B2 | 6/2009 | Sakhrani et al. | |
| 8,124,207 B2 | 2/2012 | Sakhrani et al. | |
| 2011/0313363 A1 | 12/2011 | D'Souza et al. | |

FOREIGN PATENT DOCUMENTS

| | | | | |
|---|---|---|---|---|
| EP | 1060031 B1 | | 3/2003 | |
| JP | 2005160888 A | | 6/2005 | |
| WO | WO 2007115156 A2 | * | 10/2007 | ............ A61L 31/10 |
| WO | 2009053947 A2 | | 4/2009 | |
| WO | 2010034004 A1 | | 3/2010 | |
| WO | 2011092536 A1 | | 8/2011 | |
| WO | 2012174045 A2 | | 12/2012 | |

OTHER PUBLICATIONS

Hillborg et al.; "Hydrophobicity Recovery of Polydimethylsiloxane after Exposure to Corona Discharges"; Polymer; 1998; pp. 1991-1998; vol. 39, No. 10.

* cited by examiner

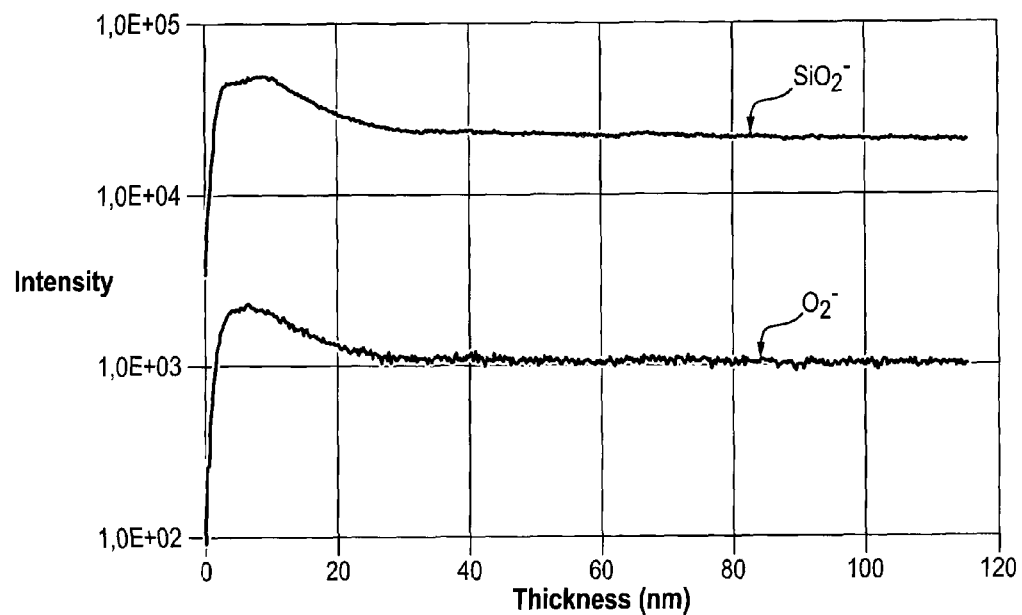
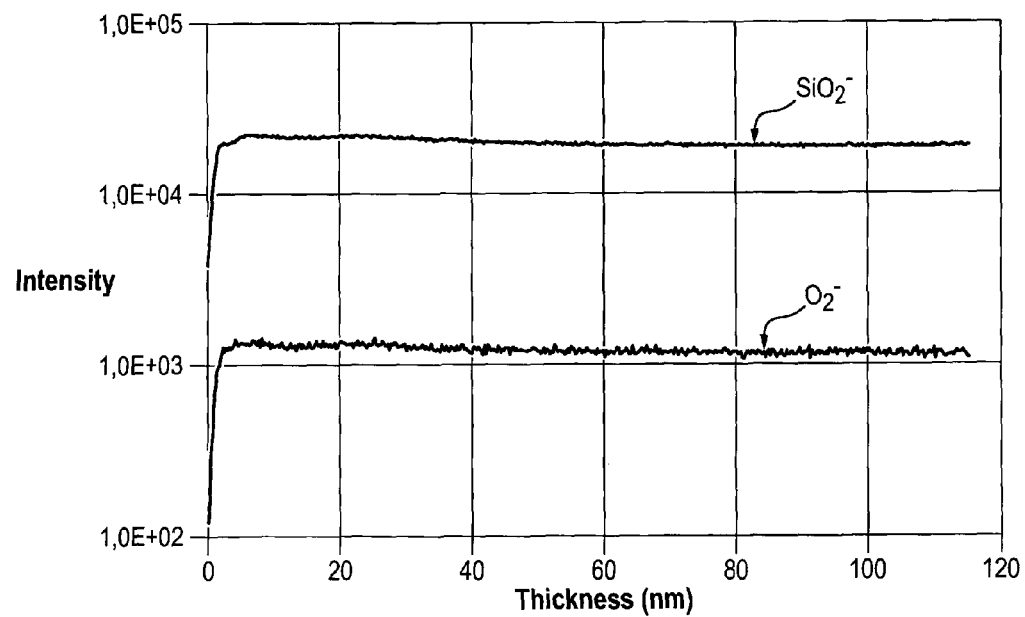

200 μm

200 μm

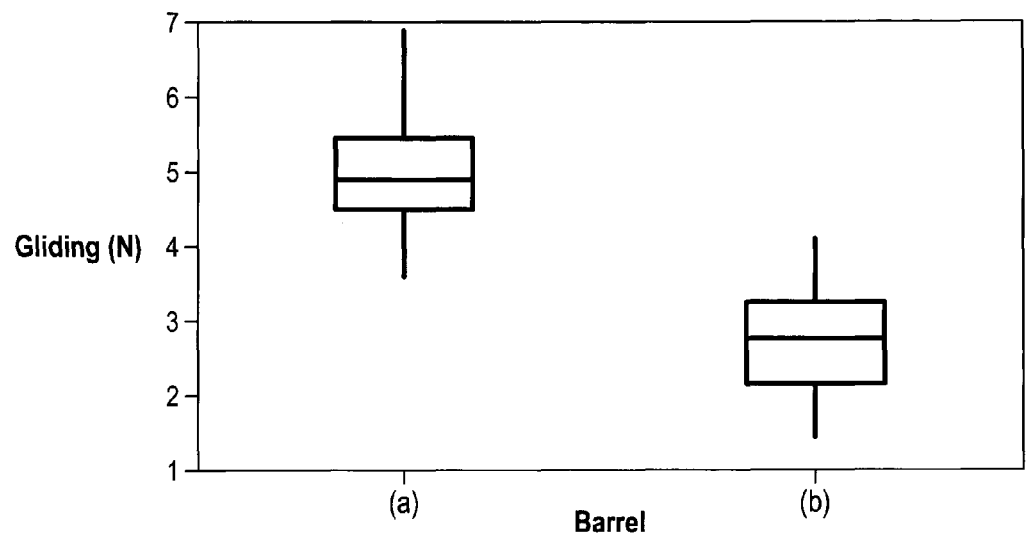
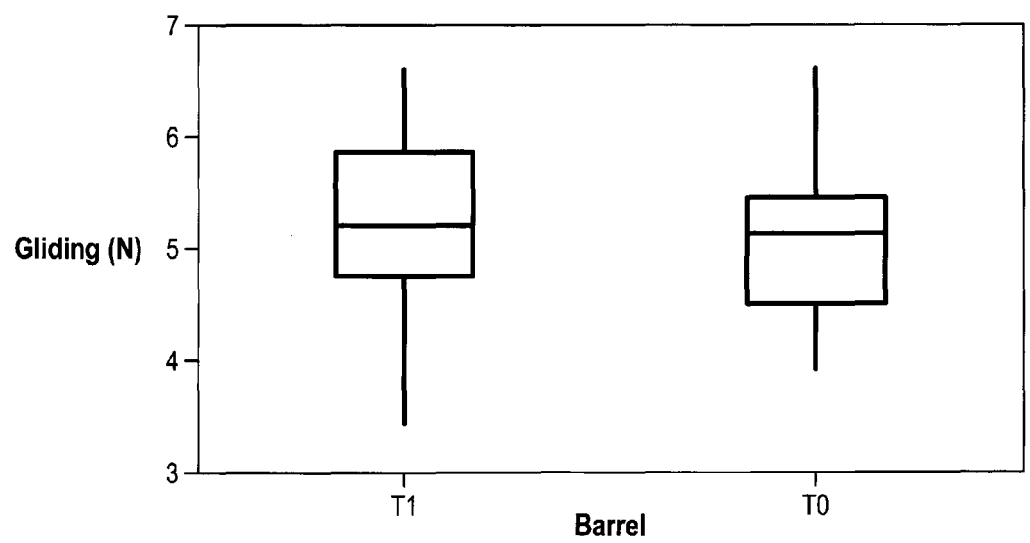

LUBRICANT COATING AND MEDICAL INJECTION DEVICE COMPRISING SUCH A COATING

CROSS-REFERENCE TO RELATED APPLICATIONS

This application is the United States national phase of International Application No. PCT/EP2013/061007 filed May 29, 2013, and claims priority to European Patent Application No. 12305592.3 filed May 29, 2012, the disclosures of which are hereby incorporated in their entirety by reference.

FIELD OF THE INVENTION

The invention relates to a lubricant coating, in particular for medical injection devices, a medical injection device comprising such a lubricant coating, and a process for manufacturing such a lubricant coating.

BACKGROUND OF THE INVENTION

Medical injection devices that comprise a sealing stopper in a gliding engagement within a container are widely used to deliver drug by injection to a patient.

Such injection devices include syringes, cartridges and auto-injectors.

Many different types of injection devices have been designed for administering medicines. Injection devices usually comprise a container intended to receive the product to be injected and a plunger rod intended to move a stopper within the container so as to expel the product therefrom at the time of injection. Empty and pre-filled disposable injection devices exist but prefilled devices are now preferred because they are more convenient and safer.

Such injection devices would be appropriate for containing new high-value drugs also commonly named "biotech" drugs that are currently developed and launched on the pharmaceutical market.

These biotech drugs can comprise for example biological elements such as proteins, peptides, DNA, RNA and the like, as well as sensitive compounds.

A major constraint with such drugs is their sensitivity towards their environment and therefore there is a need to find an appropriate container able to maintain the integrity of the drugs when they are stored for a long time in injection devices.

Traditional injection devices comprise a container made of glass or plastic and a stopper made of rubber.

Optionally, coatings can be applied on the surface of the container and/or on the surface of the stopper in order to improve the lubrication of the stopper inside the container.

But in some cases, it has been shown that such injection devices are not appropriate for long storage of high-value drugs due to the high and long term interaction with their containers.

Indeed, it has been shown that some degradations of the drug (aggregation, denaturing, unfolding, etc. . . . ) occur with time, leading to the withdrawal of the prefilled device out of the market and therefore leading to a high loss for pharmaceutical companies as well as leading to a risk for patients to be treated with degraded pharmaceutical drugs.

Therefore there is a need to have a prefilled injection device having a medical container compatible with biotech drugs, meaning a container that avoids any denaturing and/or aggregation of the drug after filling.

In addition, such prefilled injection devices should also have good gliding properties i.e. a low gliding force to move the stopper within the container.

Moreover, if a coating is applied on the surface of the prefilled injection device, the integrity of the coating has to be maintained from the deposition of the coating on the surface(s) of the medical device until the injection of the drug to the patient.

It means that any delaminating or breaking phenomena of the coating are to be avoided.

This is particularly the case for lubricant coatings that are commonly used to enhance the gliding properties of the injection devices.

Finally, the integrity of the drug, the integrity of the lubricant coating and the gliding properties of the prefilled device need to be maintained over time i.e. to be stable for at least the shelf life of the prefilled injection device.

Some documents such as U.S. Pat. No. 5,338,312 and EP 0 201 915, describe an injection device having enhanced gliding properties by using a lubricant coating that is cross-linked in order to immobilize the layer on the surface of the container of the injection device.

However, such injection devices are not necessarily compatible with sensitive drugs such as biotech drugs and/or vaccines.

Further, these documents do not address the issue of providing a coating that would keep its integrity within time and that would not have any significant or adverse interaction with the drug contained inside the injection device.

The document EP 1 060 031 describes a lubricated medical container that exhibits good gliding properties as well as low protein adsorption on the inner surface of the container.

Nevertheless, this document does not disclose any coating compatible with sensitive drugs such as vaccines and/or biotech drugs.

Indeed, as the coating described is not directed to be used with high-value drugs, even if the adsorption may be avoided, some denaturing of the drugs could occur.

This would be the case for example, with some polymers described in this document such as polymers with phosphorylcholine groups or poly-(2-hydroxyethyl methacrylate).

Additionally, this document does not disclose any information on a coating that keeps its integrity over time, after a long storage period.

However, the issue of storage is essential for prefilled syringes, as the lubricant coating needs to be stable over time not only before the filling of the drug in the injection device but also after the drug has been introduced in the injection device.

Recently, it has been demonstrated that particles can appear in the pharmaceutical composition after the filling of the container, due to interaction of the drug with the coating present on the inner wall of the container or on the surface of the stopper.

Generally speaking, silicone or silicone derivatives are often used as lubricant, and they have been identified as a main source of particle generation.

Indeed, specialists have observed that significant amounts of subvisible particles (i.e. particles having a size comprised between 0.1 µm and 100 µm) accelerate protein aggregation and unfolding.

Furthermore, sub-visible particles consisting of silicone, protein aggregates, or mixture of silicone with unfolded proteins and/or excipients may be hazardous for patients: it is thus recommended that the level of particles in this size range be carefully controlled.

One can refer in this respect to "Overlooking Subvisible Particles in Therapeutic Protein Products: Gaps That May Compromise Product Quality", by John F. Carpenter et al., Journal of Pharmaceutical Sciences, Vol. 98, No. 4, April 2009.

These recommendations have been translated in more severe norms with regard to the maximum authorized particle level defined by the United States Pharmacopeia (USP 31 <788>) and the European Pharmacopeia (EP 6 <2.9.19>).

These norms not only place a heavy burden onto the pharmaceutical companies themselves but also onto the manufacturers of injection devices, since the release of particles from the containers into the pharmaceutical composition can occur and has to be avoided or at least dramatically reduced.

A goal of the invention is thus to provide a lubricant coating that exhibits a good compatibility with sensitive drugs stored inside a coated medical injection device for long time period in order to meet the pharmacopeia norms with regard to the level of particles in the drug, while still providing good performance with regard to the gliding of the stopper within the container of the medical injection device, and keeping its integrity over time.

BRIEF DESCRIPTION OF THE INVENTION

An object of the invention is a lubricant coating for a medical injection device, comprising successively:
- a bottom layer in contact with the medical device surface of the container to be lubricated, comprising a mixture of cross-linked and non-cross-linked poly-(dimethylsiloxane),
- an intermediate layer consisting essentially of oxidized poly-(dimethylsiloxane) and having a thickness comprised between 10 and 30 nm, said thickness being measured by Time-Of-Flight-Secondary Ion Mass Spectrometry as described herein, and,
- a top layer consisting essentially of non-cross-linked poly-(dimethylsiloxane) and having a thickness of at most 2 nm, said thickness being measured by X-ray Photoelectron Spectroscopy as described herein.

"Composition consisting essentially of" means a composition that can contain, in addition to the components explicitly recited, only other components which do not materially affect the essential characteristics of the composition, such as minor amounts of impurities.

According to a preferred embodiment, the bottom layer is a gel.

Other advantageous features of the coating, taken separately or in combination, are the following:
- said coating has a thickness comprised between 90 and 400 nm;
- the thickness of the bottom layer is between 58 and 388 nm;
- the formula of the oxidized poly-(dimethylsiloxane) of the intermediate layer (51) is:

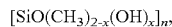
    $[SiO(CH_3)_{2-x}(OH)_x]_n$, where x ranges from 0.2 to 1.5 and n is an integer; preferably, x=0.75;
    n ranges from 70 to 100;
- the thickness of the intermediate layer is between 15 and 25 nm.

Another object of the invention is a medical injection device comprising a barrel and a stopper in gliding engagement within the barrel, characterized in that the inner wall of the barrel is at least partially covered by a lubricant coating as described above.

The gliding force of the stopper within the barrel is advantageously comprised between 1 and 8 N, preferably between 3 and 6 N, said gliding force being measured as described herein.

The barrel may be made of glass.

According to an embodiment, said medical device consists of a syringe having an internal volume of 1 ml and a diameter of 6.35 mm.

The weight of the lubricant coating may then be between 0.1 and 0.4 mg.

The particle level generated inside the device when filled with a solution of a mixture of 10 g/L of Phosphate Buffered Saline and 2.13 mg/L of Polysorbate 80 in Water for Injection and filtered with a 0.22 microns filter, is preferably less than 2.11 particles per $mm^2$ of coating when measured by light obscuration method as described herein and/or less than 10.56 particles per $mm^2$ of coating when measured by flow microscopy as described herein.

Another object of the invention is a process of manufacturing a lubricant coating as described above.

Said process advantageously comprises the following steps:
- depositing a layer of poly-(dimethylsiloxane) on a substrate, the thickness of said layer being comprised between 90 and 400 nm, measured by reflectometry as described herein,
- exposing said layer to an oxidizing plasma, so as to form said lubricant coating by oxidizing and cross-linking at least part of the poly-(dimethylsiloxane).

According to advantageous embodiments of this process, taken alone or in combination:
- the viscosity of the deposited poly-(dimethylsiloxane) is between 900 and 1200 cSt, preferably 1000 cSt at 25° C.;
- said oxidizing plasma is carried out in an atmosphere comprising oxygen and argon;
- the atmosphere of said oxidizing plasma contains oxygen and argon with respective partial pressures comprised between 15 and 30% for oxygen and between 85 and 70% for argon;
- the duration of exposure is between 10 and 40 seconds;
- the oxidizing plasma is generated by radio-frequency, with a power ranging from 50 to 300 W, and under a vacuum in the range 1.33-13.3 Pa (10-100 mTorr) in absolute value.

BRIEF DESCRIPTION OF THE DRAWINGS

Other features and advantages of the invention will be apparent from the detailed description that follows, based on the appended drawings wherein:

FIG. 3 shows the Time-Of-Flight-Secondary Ion Mass Spectrometry (TOF-SIMS) measurements for a lubricant coating according to an embodiment of the invention (graph (a)) and for a poly-(dimethylsiloxane) (PDMS) layer (graph (b)), FIG. 9 shows the gliding force of a stopper within the barrel of a syringe containing a lubricant coating according to the invention (a) and a syringe containing a PDMS layer (b), FIG. 10 shows the evolution of the stopper gliding force before and after one month of ageing (T0/T1).

DETAILED DESCRIPTION OF EMBODIMENTS OF THE INVENTION

Figure 1:
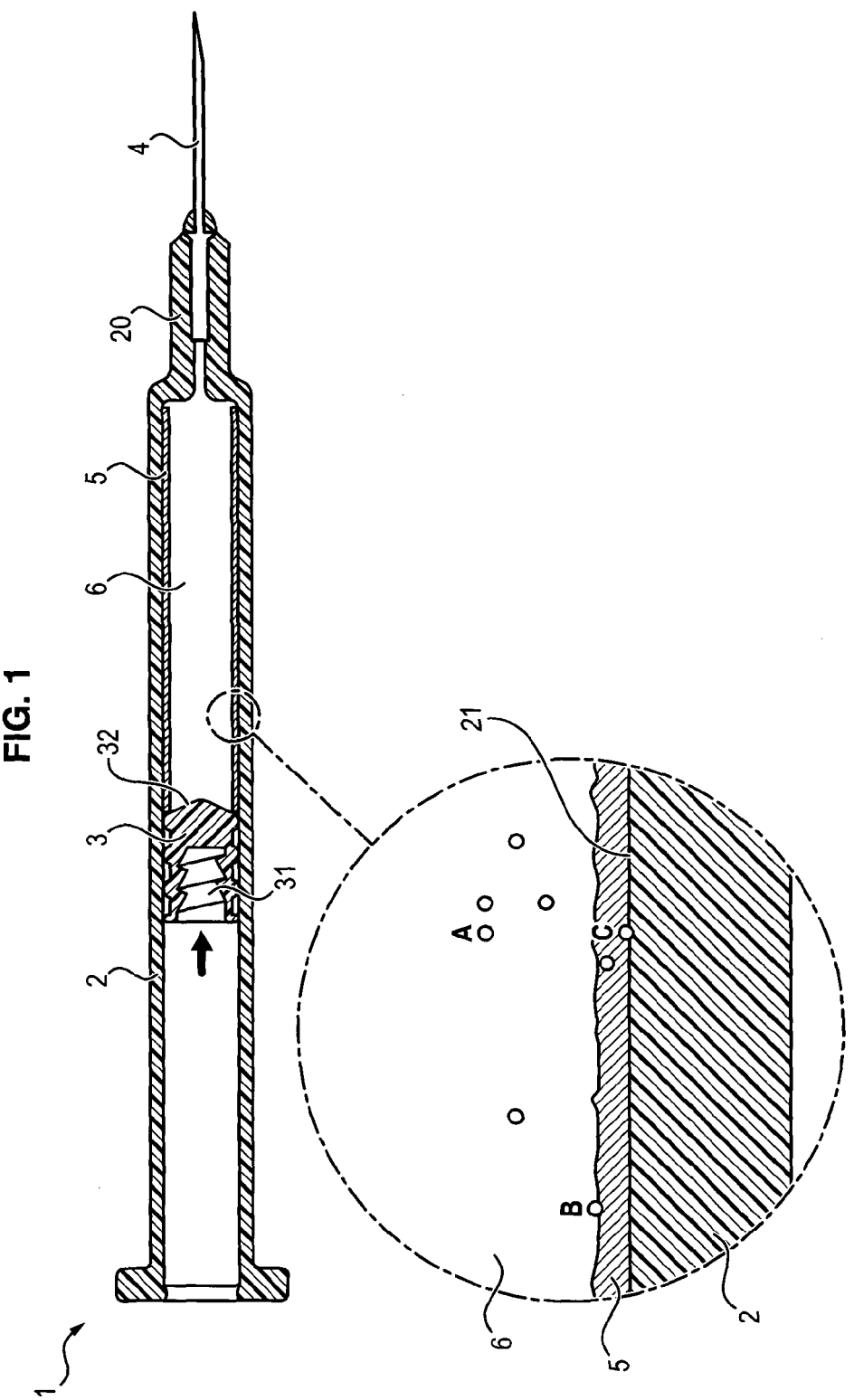
FIG. 1 is a schematic sectional view of a medical injection device according to one embodiment of the invention.

Referring to FIG. 1, the medical injection device 1 according to the present invention comprises a container, such as a barrel 2, and a stopper 3 in gliding engagement within the barrel 2.

The barrel 2 of the injection device may be made of any kind of glass or plastic suitable for medical applications.

The stopper 3 may be made of any elastomeric material, e.g. rubber, butyl rubber, silicone rubber or a mixture.

The stopper 3 may be adapted to be connected for example to a plunger rod of a syringe or to a plunger rod of an injection pump, the connection being done by any suitable connecting means, e.g. a threaded portion 31, etc.

The tip 20 of the barrel 2 opposed to the stopper 3 may be luer-type in order to be connected to a needle hub, a cap or a catheter, or may comprise a needle 4.

In the present invention, the inner wall 21 of the barrel 2 is coated with a lubricant coating 5.

This medical device may be a prefilled injection device, such as syringe, a cartridge or an auto-injector that may contain a pharmaceutical composition 6 that can be a high-value drug, i.e. a vaccine or a biotech drug.

Figure 2:
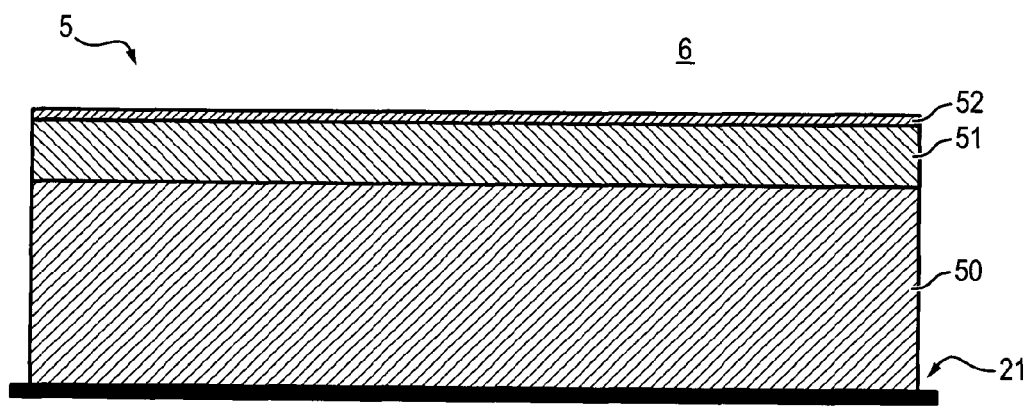
FIG. 2 shows a sectional view of a lubricant coating according to a preferred embodiment of the invention.

The lubricant coating 5 present on the inner wall 21 of the medical device can be represented as shown on FIG. 2. This figure shows a sectional view of a lubricant coating according to a preferred embodiment of the invention.

The inner wall 21 may be planar, curved, or have any other geometry.

The lubricant coating 5 comprises a bottom layer 50 in direct contact with the inner wall 21 of the barrel 2, an intermediate layer 51 and a top layer 52 in contact with the pharmaceutical composition 6 contained within the medical device.

The bottom layer 50 comprises a mixture of cross-linked and non-cross-linked poly-(dimethylsiloxane), commonly named PDMS.

Preferably, said bottom layer has a gel structure, i.e. a three-dimensional solid network provided by the cross-linked poly-(dimethylsiloxane) that retains a liquid phase corresponding to the free non-cross-linked poly-(dimethylsiloxane).

Above the bottom layer 50, the intermediate layer 51 consists essentially of oxidized poly-(dimethylsiloxane) and has a thickness comprised between 10 and 30 nm.

Preferably, this oxidized PDMS is characterized by a higher ratio of oxygen regarding PDMS, meaning an increase of around 4.5% below the usual rate of oxygen present in PDMS, as well as a smaller ratio of carbon, i.e. a decrease of around 4.5% below the usual rate of carbon present in PDMS.

Preferably, the chemical formula of the intermediate layer 51 may advantageously be:

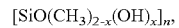

$[SiO(CH_3)_{2-x}(OH)_x]_n$, where x ranges from 0.2 to 1.5.

In a preferred embodiment, x ranges from 0.6 to 1 or more precisely, x is equal to 0.75.

Furthermore, as the measure of the degree of polymerization n can be sometimes challenging due to the specific geometry of the medical device and the low quantity of material in the lubricant coating, the n value is estimated to be comprised from 70 to 100 or more precisely, n is estimated to be around 85.

Above the intermediate layer 51, the lubricant coating 5 comprises a top layer 52 consisting essentially of poly-(dimethylsiloxane) and having a thickness of at most 2 nm.

Preferably, the top layer 52 shows neither cross-linkage nor oxidation, and its chemical composition is substantially similar to pure PDMS.

Said top layer 52 is thus in contact with a pharmaceutical composition 6 contained in the medical device.

The thickness of the lubricant coating 5 can range from 50 to 1000 nm. According to a preferred embodiment, the thickness of the lubricant coating 5 is comprised between 50 and 500 nm.

Due to the specific composition of these three different layers, the lubricant coating 5 according to the present invention generates a very low level of particles in the pharmaceutical composition 6 while maintaining very good mechanical performances.

Indeed, there is a direct relationship between the number of particles and the surface of the coating as the particles can be generated by the interaction of the pharmaceutical composition 6 with the lubricant coating 5.

Therefore, the larger the surface of the coating is, the higher the amount of particles will be.

It has been shown that with the coating according to an embodiment of the invention, the level of particles present in the pharmaceutical composition is below 2.11 particles per $mm^2$ of lubricant coating surface when measured by HIAC and below 10.56 particles per $mm^2$ of lubricant coating surface when measured by MFI™.

As shown on FIG. 1 different particles can be generated over time when a medical injection device is filled with a pharmaceutical composition and keep under storage condition. For example, silicone particles A (e.g. droplets) can be released from the coating present on the inner wall of the medical device into the pharmaceutical composition.

The particles can also be aggregates or denatured drugs (referred as B on FIG. 1) that are present in the pharmaceutical composition and that have been formed by the interaction of the pharmaceutical composition with silicone particles A and/or with the lubricant coating.

A third category of particles (referred to as C) can be released in the pharmaceutical solution due to the mechanical friction of the stopper along the wall of the barrel.

With the lubricant coating 5 according to the invention, the level of particles generated by the lubricant coating is significantly reduced, which implies that the level of sub-visible particles that may be released into the pharmaceutical composition or be in contact with the pharmaceutical composition during the life of the injection device is reduced.

As a consequence, the risk of aggregation of proteins in the solution itself, due to the adsorption generated by the surface of the silicone droplets, as well as the risk of adsorption of proteins at the surface of the barrel is significantly reduced.

Therefore, the pharmaceutical composition stored in the medical injection device remains stable over time as neither aggregation nor denaturing of the drugs due to potential interaction with the coating present on the inner surface of the container occur.

Further, since silicone particles are likely to be released in a very small amount into the pharmaceutical composition, they do not generate any background noise that would be detrimental to the monitoring of protein aggregation. Additionally, as particles formed by silicone or denatured drugs are believed to present toxicity when injected into a living organism, the coating of the present invention leads to minimize the risk of contamination of the patient.

The lubricant coating applied on the inner wall of a medical container in accordance with the present invention also shows favorable mechanical properties. For example, no delaminating or break-up of the coating occurs under energetic movement (for example during transportation), as well as under dramatic changes in temperature. Indeed, the coating remains stable when applied on the inner wall of the container without any release of elements.

A further effect in accordance with an embodiment of the present invention is that the above-mentioned technical effects i.e. good gliding properties and favorable mechanical properties, remain stable during a long period of time, for example from 12 to 24 months or more.

This is particularly important when the medical container is filled with a pharmaceutical composition and is stored in different conditions and positions, is transported over long distances and then finally used to inject the pharmaceutical composition into a patient after a long period of storage.

Another advantage of an embodiment of the invention is that no further chemical species are introduced within the medical container, since the single chemical compound consists in a classic silicone oil, already used and authorized for medical use that leads to lower the risk of unpredictable side effects.

When expressed in term of particles per $mm^2$ of lubricant coating surface, the particle level generated by an embodiment of the invention is below 2.11 particles/$mm^2$ if measured by HIAC or below 10.56 particles/$mm^2$ if measured by MFI™. As a result, the obtained medical injection device fulfills the above mentioned requirements, i.e. a high compatibility with vaccines and biotech drugs, good gliding performance, favorable mechanical properties and maintenance of these properties over a long period of time (e.g. 12 to 24 months).

If the amount of particles present in a container having a lubricant coating according to the present invention is compared to the amount of particles present on a similar container having a pure silicone oil coating, the above values correspond respectively to a reduction of particles of at least 70% when measured by HIAC, and of at least 90% when measured by MFI™.

The lubricant coating 5 is advantageously formed by deposition of a layer of poly-(dimethylsiloxane) on the inner wall 21 of the medical injection device, followed by the exposure of said layer to an oxidizing plasma.

The deposition may be accomplished by any suitable technique, e.g. spraying, dipping, spin coating, etc. in order to obtain a layer thickness comprised between 50 and 1000 nm, depending of the surface and the type or material of medical injection device.

According to a preferred embodiment, the viscosity of the deposited PDMS is comprised between 900 and 1200 centistokes (cSt), preferably 1000 cSt, at 25° C.

The plasma treatment is carried out in an oxidizing atmosphere.

According to a preferred embodiment, the atmosphere is a mixture of 15 to 30% of oxygen and 85 to 70% of argon. Unless otherwise specified, the composition of the atmosphere of the plasma treatment is expressed herein in terms of respective partial pressures. More preferably, the atmosphere comprises 25% of oxygen and 75% of argon.

Generally speaking, plasma may be produced by different techniques such as corona discharge, microwave, radio-frequency or any other convenient method. However, the present invention is manufactured by a, radio frequency plasma treatment, i.e. with a frequency ranging from 10 to 20 MHz, preferably from 11 to 14 MHz.

The power applied to generate the plasma may be comprised between 50 and 300 W, preferably between 100 and 250 W.

The plasma treatment may be carried out at room temperature (i.e. 25° C.) and under a vacuum ranging from 1.33 to 13.3 Pa (10 to 100 mTorr) in absolute value.

The exposure time is typically comprised between 10 to 40 seconds.

Of course, the above parameters depend on the plasma reactor geometry, the surface and volume of the medical device comprising the lubricant coating, the arrangement of the devices inside the plasma reactor, the thickness of the lubricant layer, etc.

As a consequence, tiny changes in parameters can lead to a very different coating and the skilled person may select the parameters of the plasma treatment in order to optimize the treatment depending on the equipment used as well as on the devices to be treated.

Plasma Treatment for 1 ml Long Glass Syringes

For a 1 ml long syringe having a glass barrel, the preferred conditions of the plasma treatment (hereinafter designated by the term "1 ml long plasma treatment") are:
  plasma type: capacitively coupled plasma driven by a radiofrequency power supply at 13.56 MHz;
  treatment time: 30 s;
  power: 200 W;
  pressure: 8 Pa (0.06 Torr);
  atmosphere: 15/75 sscm of $O_2$ and Ar respectively.

This treatment is applied to a syringe containing a lubricant coating having a weight of 0.4 mg.

Structure of the Lubricant Coating

The oxidizing plasma has the effect of oxidizing and cross-linking at least part of the poly-(dimethylsiloxane) deposited on the medical injection device surface, therefore forming a lubricant coating according to the present invention.

Since the plasma treatment does not substantially modify the thickness of the lubricant coating, the thickness of the deposited PDMS layer is chosen depending on the required thickness of the lubricant coating.

The effect of an oxidizing plasma on a PDMS layer has been partially described by H. Hillborg et al in "Hydrophobicity recovery of polydimethylsiloxane after exposure to corona discharge", Polymer, Vol. 39, No 10, pp. 1991-1998, 1998.

A film comprising PDMS with a thickness of 1.6 mm was formed on a substrate and subjected to a corona discharge of 1.5 or 2.6 W during 20 minutes to 200 hours.

It was shown that the resulting film had an oxidized surface in the form of a silica-like layer having a thickness from 8 to 10 nm, leading to a reduction of the hydrophobicity of the film.

However, a recovery of the hydrophobicity was observed after some time.

Indeed, as explained in this document, some non-cross-linked PDMS situated below the oxidized layer was able to migrate toward the surface of the film through cracks and fissures in the oxidized layer, due to the brittleness of this oxidized layer.

Although the lubricant coating according to embodiments of the invention is much thinner than the film formed by Hillborg et al, and the conditions of the plasma treatment are substantially different from their corona discharge, it is believed that a similar phenomenon explains the presence of the top layer 52 consisting of non-cross-linked PDMS above the oxidized intermediate layer 51.

The thickness of the top layer 52 may vary with the treatment duration.

Indeed, said thickness is substantially null immediately after the exposure to the oxidizing plasma, and increases with time until reaching a thickness of about 2 nm.

The composition and structure of the bottom layer 50, intermediate layer 51 and top layer 52 have been investigated in detail using several techniques.

Composition of Top and Intermediate Layers

The composition of the top and the intermediate layers in silicon, oxygen and carbon has been analyzed by X-ray Photoelectron Spectroscopy (XPS).

A Surface Science SSX-100 electron spectrometer was used for this experiment by using widths, areas and binding energies of Si (2p), O (1s) and C (1s).

The samples were tilted in order to achieve different analysis depths and three angles were used (10, 35 and 60°) for allowing an analysis at different depths, respectively about 2, 5 and 10 nm from the surface.

The samples were prepared as explained below.

Small samples of glass (about 0.4*0.4 cm) were cut from each glass barrel before deposition of any coating. The samples were washed with water to remove dust and dried. Then, the clean samples were re-assembled with adhesive tape to form the original barrel.

A first set of barrels was then coated with a lubricant coating 5 according to the present invention: they were siliconized with 0.25 mg of silicone Dow Corning PDMS 1000 cSt before being stored during one week and then submitted to a plasma treatment with a frequency of 13.56 MHz, a power of 200 µl, a vacuum of 1.33 Pa (10 mTorr) and a exposure time of 30 seconds.

A second set of barrels was just siliconized with 0.25 mg of silicone Dow Corning PDMS 1000 cSt.

Thereafter, the pre-cut samples were disassembled and analyzed separately.

|  | % C | % O | % Si | % O/% C |
|---|---|---|---|---|
| PDMS | 49.9 | 23.9 | 26.2 | 0.5 |
| Top layer 52 (Angle 10° - 2 nm) | 45.4 | 22.6 | 32.0 | 0.5 |
| Intermediate layer 51 (Angle 35° - 5 nm) | 40.5 | 32.6 | 26.9 | 0.8 |
| Intermediate layer 51 (Angle 60° - 10 nm) | 44.6 | 28.6 | 26.8 | 0.6 |

The above table shows the results of the chemical composition and the oxidation ratio oxygen regarding carbon (% O/% C) of PDMS, the top layer 52 and the intermediate layer 51 of the lubricant coating 5 present on the different samples.

The top layer 52 has been analyzed at its maximum depth meaning at 2 nm from the top surface (i.e. from the pharmaceutical composition 6) and shows a percentage of oxygen substantially similar to the percentage of oxygen present in PDMS, namely 22.6% and an oxidation ratio of 0.5. The chemical composition and the oxidation ratio of the top layer 52 are advantageously close or similar to the composition and oxidation ratio of PDMS, as this top layer is in direct contact with the stopper 3 and plays a key role to achieve good mechanical and gliding performances.

Indeed, PDMS is known to be a good lubricant with a low viscosity rate and good gliding performances.

The analysis of the intermediate layer 51, analyzed at two different depths 5 nm and 10 nm from the top surface shows that this layer 51 at least partially oxidized: it presents a significant higher percentage of oxygen, i.e. 28.6%, which is around 4.75% higher than PDMS and an oxidation ratio of at least 0.6

The presence of free PDMS chains at the surface of the treated samples reveals that the oxidized layer 51 is porous and allows diffusion or migration of unreacted silicone chains from the bottom layer 50 to the surface.

This is consistent with contact angle measurements as it will be seen below.

Moreover, according to this analysis, it has been noticed that the oxidation ratio of the intermediate layer 51 is between 0.6 and 5, preferably between 0.8 and 2, or more precisely 1.4.

Furthermore, the average formula of the intermediate layer 51 may advantageously be as follows:

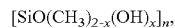

$$[SiO(CH_3)_{2-x}(OH)_x]_n,$$

where x ranges from 0.2 to 1.5.

In a preferred embodiment, x ranges from 0.6 to 1 or more precisely, x is equal to 0.75.

Furthermore, as the measure of the degree of polymerization n can be sometimes challenging due to the specific geometry of the medical device and the low quantity of material in the lubricant coating, this n value is estimated to be comprised from 70 to 100 or more precisely, n is estimated to be around 85.

This intermediate layer 51 plays a key role to limit the generation of particles in the pharmaceutical composition.

Indeed, this intermediate layer acts as a brittle barrier to prevent direct interaction between the pharmaceutical composition and the bottom layer which essentially consists of free PDMS.

Therefore, free PDMS cannot diffuse massively into the pharmaceutical composition.

Only a limited amount of free PDMS can migrate through this intermediate layer to form the thin top layer 52.

Then, this top layer 52 remains strongly linked to the intermediate layer 51 by intermolecular bonds, and does not generate high amount of particles.

Moreover, mechanical properties are enhanced since this intermediate layer 51, contributes substantially to the lubricant coating rigidity.

As this oxidized layer has a glass-like structure, the hydrophobicity of the lubricant coating surface is also limited, hence enhancing its compatibility with biotech drugs and vaccines.

Finally, this brittle intermediate layer can be easily deformed by the movement of a stopper inside the coated barrel, which allows sufficient lubrication for preserving the gliding properties.

Thickness of the Intermediate Layer

The thickness of the oxidized intermediate layer has been measured by TOF-SIMS technique: this technique performs the erosion of a surface by an ion-beam and the secondary ions produced during the erosion process are analyzed. TOF-SIMS profiles have been performed at different locations on the barrel of a 1 ml long glass syringe on samples coated with a lubricant coating 5 or samples coated with PDMS.

A $Bi_3$ analytical source at 25 kV was used together with a Cs abrasion source at 500 V and the pressure in the analytical chamber was less than $5 \times 10^{-9}$ Torr.

The analysis has been carried out from the coating surface towards the thickness of the glass barrel.

To that end, samples were prepared as follows.

Small samples of glass (about 0.4*0.4 cm) were cut from each glass barrel before deposition of any coating. The samples were washed with water to remove dust and dried. Then, the clean samples were re-assembled with adhesive tape to form the original barrel.

A first set of barrels was then coated with a lubricant coating according to the present invention: they were siliconized with 0.25 mg of silicone Dow Corning PDMS 1000 cSt before being stored during one week and then submitted to a plasma treatment with a frequency of 13.56 MHz, a power of 200 W, a vacuum of 1.33 Pa (10 mTorr) and a exposure time of 30 seconds.

A second set of barrels was only siliconized with 0.25 mg of silicone Dow Corning PDMS 1000 cSt.

Thereafter, the pre-cut samples were disassembled and analyzed separately.

As the TOF-SIMS techniques gives a quantity of secondary ions as a function of an erosion time, a calibration was realized in order to correlate the erosion time with the coating thickness. To that end, the hypothesis was made that the erosion time of a 1000 cSt PDMS layer and the one of the lubricant coating 5 were substantially similar.

A calibration sample was performed by using a PDMS layer deposited by spin coating on a glass surface.

The layer thickness of this calibration sample was measured by ellipsometry and the erosion time for the whole layer was measured by TOF SIMS. It has been found that 43.2 seconds of erosion time are equivalent to 10 nm of PDMS.

FIG. 3 shows the results of the TOF SIMS measurements carried out on the lubricant coating 5 (graph (a)) and a PDMS layer (graph (b)). This FIG. 3 represents the intensity of the secondary ions $SiO_2^-$ and $O_2^-$ depending on the thickness of the layer (from the top surface in contact with the pharmaceutical solution 6 to the bottom surface in contact with the barrel inner wall 21).

A peak with a maximum near 5 nm can be seen on graph (a) for $SiO_2^-$ and $O_2^-$. This means that the intermediate layer is highly oxidized. On the contrary, no peak can be seen on the graph (b) for the same secondary ions, corresponding to a PDMS layer.

According to these data, it can be concluded that the thickness of the intermediate layer 51 is comprised between 10 and 30 nm, preferably between 15 and 25 nm. These values are significant as a thinner intermediate layer (below 10 nm) would not significantly prevent the generation of particles into the pharmaceutical solution while a thicker layer (higher than 30 nm) could lose its mechanical properties and demonstrate poor gliding performances.

Thickness of the Lubricant Coating

The thickness of the lubricant coating according to the present invention has been measured by reflectometry with a RapID equipment (namely a Silicone Layer Explorer Apparatus) and compared to a PDMS layer.

Prior to the measurements, a calibration of the apparatus was required on a bare glass barrel (i.e. without any silicone), with a focus all along the barrel length.

Each coating, either a PDMS layer or a coating according to the present invention, has been deposited on a 1 ml long bare glass barrel. The thicknesses were compared and correlated with the particle level generated, the mechanical performances and the mechanical properties.

It has been found that a layer thickness between 50 and 500 nm, more precisely between 90 and 400 nm was optimal to fulfill these requirements with such syringe.

In this embodiment, the average thickness of the lubricant coating thickness was found to be 150 nm.

Finally, it has been shown that the coating thickness is not modified during the coating formation.

Wettability of the Lubricant Coating Surface

The wettability of the surfaces has been studied with a goniometer and Water For Injection (WFI).

The measurements of water angles were performed on lubricant coatings according to the present invention after 3 days and 7 days of storage at room temperature, in order to analyze the evolution of their hydrophobic properties over time.

The table below summarizes the values of water angles obtained from this experiment by comparison with values obtained with a 1000 cSt PDMS layer.

| Sample | Water angle with pure water |
|---|---|
| PDMS | 100-110° |
| Lubricant coating 5 (3 days after treatment) | 27-30° |
| Lubricant coating 5 (7 days after treatment) | 50-54° |

The first line of the table shows a very high water angle between 100 and 110° for PDMS, which demonstrates that this silicone oil is very hydrophobic.

After manufacturing and a short storage time (3 days in this experiment), the lubricant coating 5 showed a very low water angle value meaning that its surface is very hydrophilic.

After a longer storage time (7 days from the treatment), an increase of the water angle is observed, corresponding to a hydrophobicity recovery of the surface of the lubricant coating 5. It is then assumed that a tiny quantity of PDMS is able to flow from the gelified bottom layer 50 through the porous intermediate layer 51, therefore forming the top layer 52.

As a result, after a short storage time (around one week), the lubricant coating 5 as described above is definitely formed and presents a moderate hydrophilic surface, which allows for reduction of the interaction with biotech drugs such as proteins and then limitation of the aggregation and denaturing phenomena.

Gel Structure of the Bottom Layer

The gel structure of the bottom layer 50 has been demonstrated by forming a scratch in the lubricant coating and by observing the behavior of the resulting lubricant coating by optical microscopy with ×20 magnification.

Figure 4A:
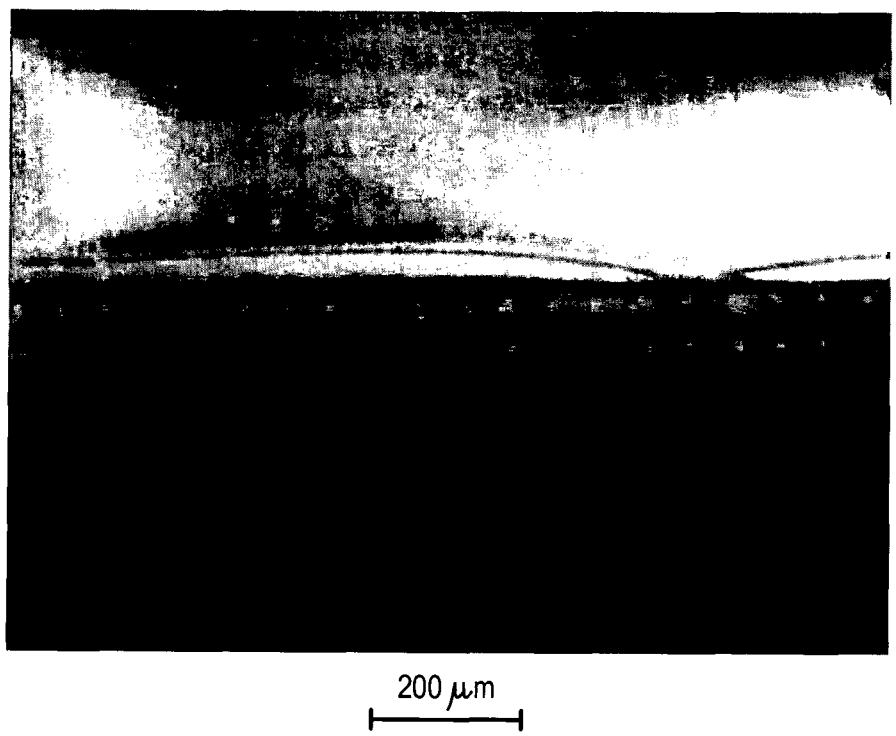
FIG. 4 shows optical microscopy images of a PDMS layer (image (a)) and of a lubricant coating according to an embodiment of the invention (image (b)) after manual scratching.
Figure 4B:
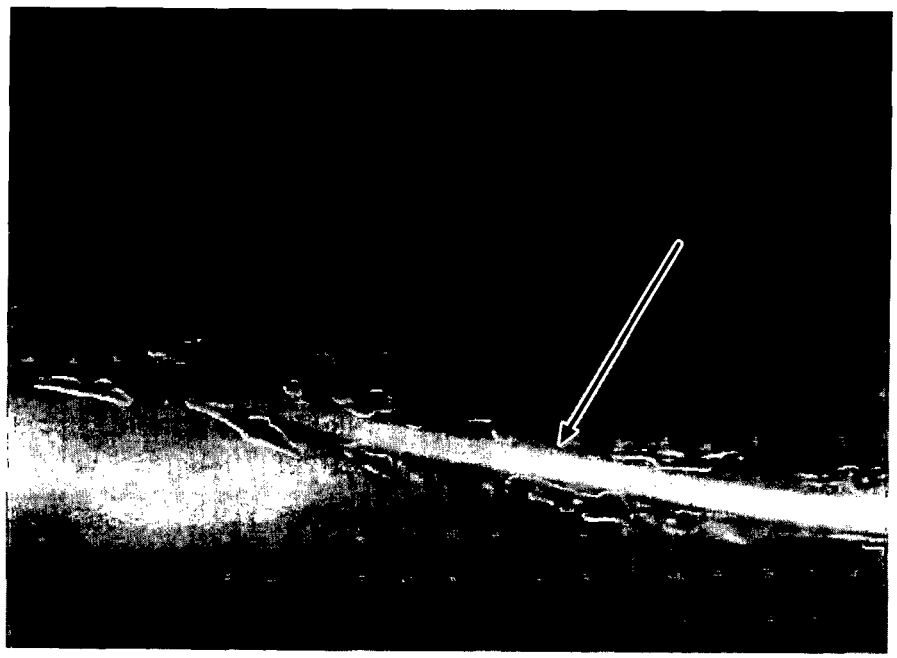

FIG. 4 shows the images obtained after a manual scratch of a PDMS layer (picture (a)) and manual scratch of the lubricant coating according to the invention (picture (b)), both layers having the same thickness.

On picture (a), the scratch was not visible since the standard PDMS layer has a viscous liquid structure, which allows the natural rearrangement of the layer which leads to the disappearance of the scratch.

By contrast, a scratch made on the lubricant coating 5 (shown by the arrow on picture (b)) remained visible over time. This demonstrated that the lubricant coating 5 is a stable and solid coating due to the presence of its gel bottom layer 50.

As no additional elements have been added during the manufacturing process, this gel bottom layer 50 can be analyzed as a network made of solid cross-linked PDMS and liquid PDMS.

The top and intermediate layers (51, 52) have a global thickness of at most 32 nm, while the optimal total thickness of the coating for a 1 ml long syringe is at least 90 nm.

The thickness of the bottom layer 50 is inferred from the difference between the total thickness and the thickness of top and intermediate layers.

Therefore the thickness of the bottom layer 50 is at least 58 nm, up to 388 nm: this layer is the thicker layer of the coating.

The liquid PDMS within the gel network allows the formation of the top layer 52, and therefore provides sufficient gliding properties.

The bottom layer 50 also prevents the release of silicone particles into the pharmaceutical composition 6 by trapping most of the liquid PDMS into the solid gel network.

Moreover, this bottom layer 50 is in direct contact with the inner wall 21 of the barrel 2, and is therefore essential for mechanical properties.

Indeed, its gel structure prevents delamination of the lubricant coating i.e. detachment from the inner wall surface, as well as break-up of the brittle intermediate layer, that should occur upon energetic movement during transportation or dramatic temperature change.

Particles Measurement (HiAc and MFI™)

The advantages of the lubricant coating according to embodiments of the invention have also been demonstrated by the measurement of the level of particles in a solution contained in the medical injection device 1 and by the measurement of the gliding force of the stopper 3 within the barrel 2 as it will be described below.

To measure the level of particles generated by the lubricant coating 5, a syringe 1 with a coating 5 according to the present invention was filled with a solution and the level of particles released in said solution was measured.

Said solution was a mixture of 10 g/L of Phosphate Buffered Saline and 2.13 mg/L of Polysorbate 80 (e.g. Tween™ 80) filtered with a 0.22 microns filter (e.g. Stericup™ filter).

The Phosphate Buffer Saline was purchased from Sigma Aldrich under reference P4417. One tablet dissolved in 200 ml of deionized water yields 0.01 M phosphate buffer, 0.0027 M potassium chloride and 0.137 M sodium chloride, with a pH of 7.4 at 25° C.

After 2 hours of storage, the solution was introduced in different 1 ml long glass barrels.

Once the barrels were closed, the filled syringes were stirred during 48 h before measuring the particle level.

Different methods and equipments may be used depending on the size of the particles to be detected and quantified.

In this case, the particles to be analyzed have a size between 1 µm to 100 µm, preferably between 1 µm and 10 µm. They are usually detected by optical devices and are called "subvisible particles" to the contrary of the so-called "visible particles" that have a size above 100 µm and can be seen with a human eye.

For such subvisible particle sizes, the most suitable counting methods are Light Obscuration (LO) or Micro Flow Imaging (MFI™), both of these technologies being described in detail below.

Light obscuration is routinely used to detect and measure subvisible particles present in parenteral solutions i.e. solutions to be injected in a living body.

Figure 5B:
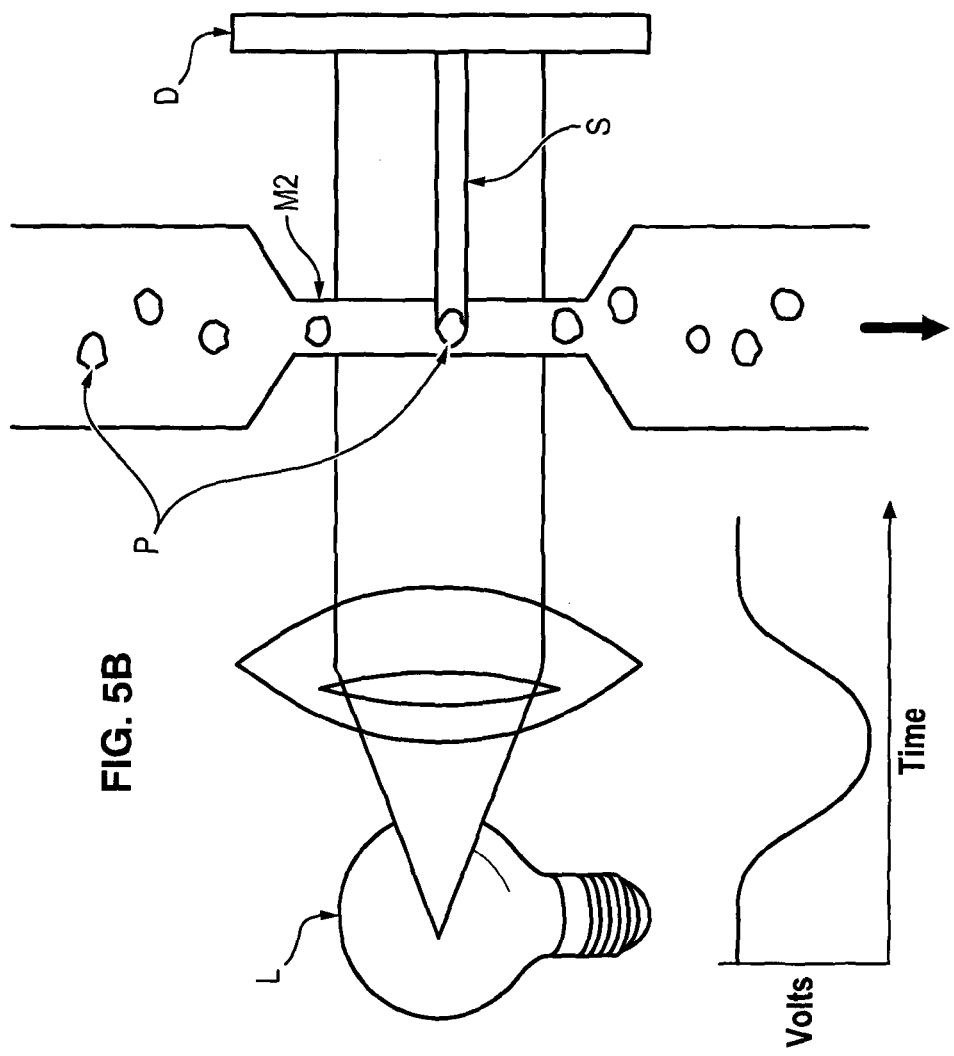
FIGS. 5A and 5B are schematic drawings illustrating the Light Obscuration method (HIAC)

As illustrated on FIG. 5B, when a particle P transits the measurement zone MZ in the direction of the arrow, it obscures (shadow S) an optical beam (e.g. generated by a light source L such as a laser diode with a wavelength of 680 nm), which results in a change in signal strength at a detector D. This signal change is then equated to the diameter of an equivalent spherical particle based on a calibration curve created using polystyrene spheres with known diameters.

Devices based on this technique are sold under the brand HIAC by Hach Lange, for example.

Advantages of such light obscuration devices are that they are easy to use, automated and fast. The measured particles size range with such devices is typically comprised between 2 and 400 µm.

To provide accuracy, the device has to be used with a large volume of solution i.e. more than 3 ml, which is greater than the volume of a small size syringe. This implies that 1 to 3 ml containers cannot be analyzed one by one.

Figure 5A:
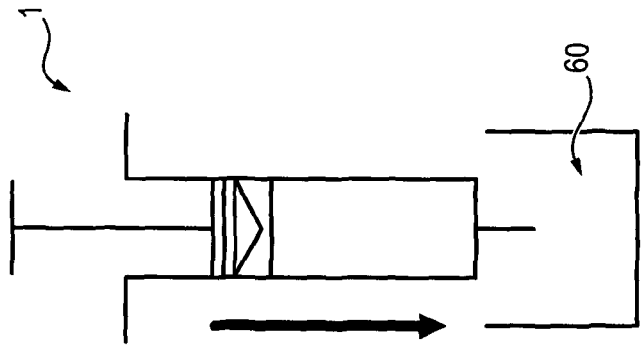

Therefore, as illustrated on FIG. 5A, several medical containers 1 (only one is shown in the figure) have to be flushed in an intermediate larger container 60 (e.g. a beaker) and the content of said intermediate container 60 is then analyzed with the light obscuration device. For conducting the analysis, the HIAC equipment was first cleaned with a mixture of Water For Injection (WFI) and isopropanol alcohol (50/50 proportion), then with WFI. All the glasswares used were also cleaned with WFI in order to reduce the concentration of particles having a size of 10 µm under 1 particle/ml.

Then, the pharmacopeia norms have been applied on the above-described solution flushed from the containers. This means that the stopper was moved into the barrel towards the distal direction in order to eject the solution through the nozzle of the medical container into the intermediate container 60.

The analysis of the samples according to the present invention consisted in four runs of at least 3 ml: the first run was used for cleaning and then discarded, while the three following runs were used for the measures. Then 3 ml of WFI were used for washing.

In the case of 1 ml medical container, several devices have been flushed into a common recipient 60 in order to obtain the required analysis volume.

A second technique used for particle measurement is Micro-Flow Imagine™ (MFI™). This is a flow microscopy method which operates by capturing images of particles in a flowing stream. For example, the equipment MFI™ DPA4200 sold by Brightwell Technologies can be used.

Figure 6B:
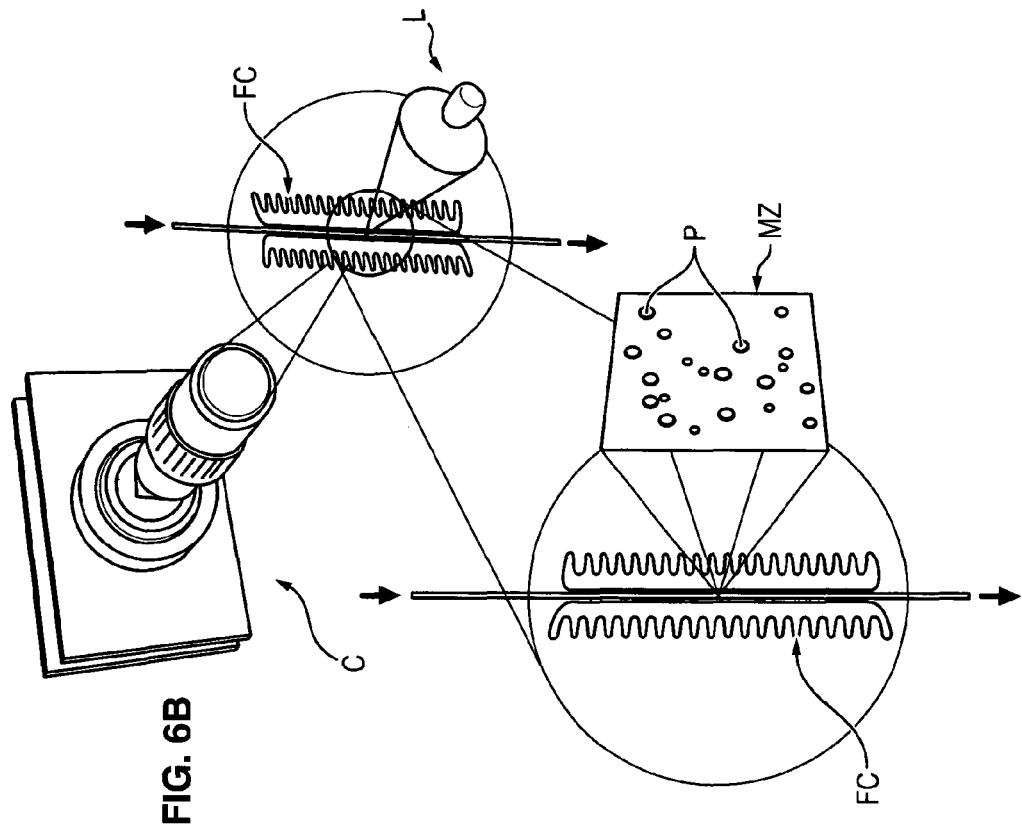
FIGS. 6A and 6B are schematic drawings illustrating the Micro-Flow Imagine™ (MFI™) method.

As illustrated in FIG. 6B, a solution to analyze is pumped from a container and goes through a flow cell FC where it is enlighten by a light L.

A camera C acquires several pictures of a small zone MZ of the flow cell FC with a known frame rate and different magnification set-points.

Each picture is automatically compared with a calibrated background, a difference in pixel contrast revealing a particle P.

The detected particle is then digitally imaged to obtain supplementary characteristics (size, shape, etc.).

Due to particle imaging, an advantage of this device is that it differentiates an air bubble from a silicone oil droplet. Moreover, it is also possible to build a particle database including count, size, transparency and shape parameters in order to analyze particle size distributions and isolate subpopulations using any measured parameters.

The measured particles size range is typically between 1 and 100 μm.

The operating protocol was the following.

First, the flow cell integrity was checked to ensure accuracy of the measurements.

Then, the cleanliness of the flow cell and the tubing was controlled with a blank run performed with WFI (the particle number has to be below 100 particles/ml).

A run with certified beads (e.g. with a size of 5 or 10 μm and with a concentration of 3000 particles/ml) could also be carried out for the calibration.

The measurement analysis of the samples according to the present invention consisted in 0.5 ml runs separated by 0.2 ml washings.

Unlike the analysis protocol performed with Light Obscuration, single 1 ml syringes were analyzed in this case.

Figure 6A:
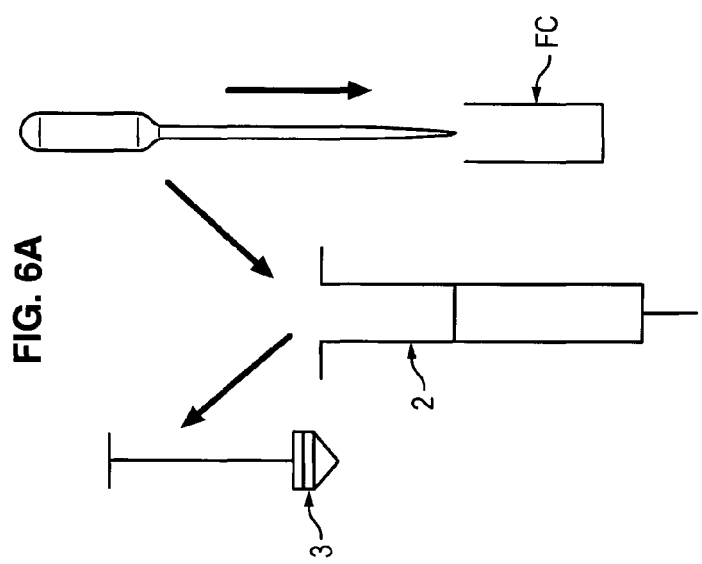

Indeed, as shown on FIG. 6A, the stopper 3 of each syringe to analyze was removed and 0.5 ml of solution was taken from the syringe barrel 2 to be introduced into the equipment.

A rinsing step was performed between each analysis, such steps being crucial for measurement accuracy.

Figure 7:
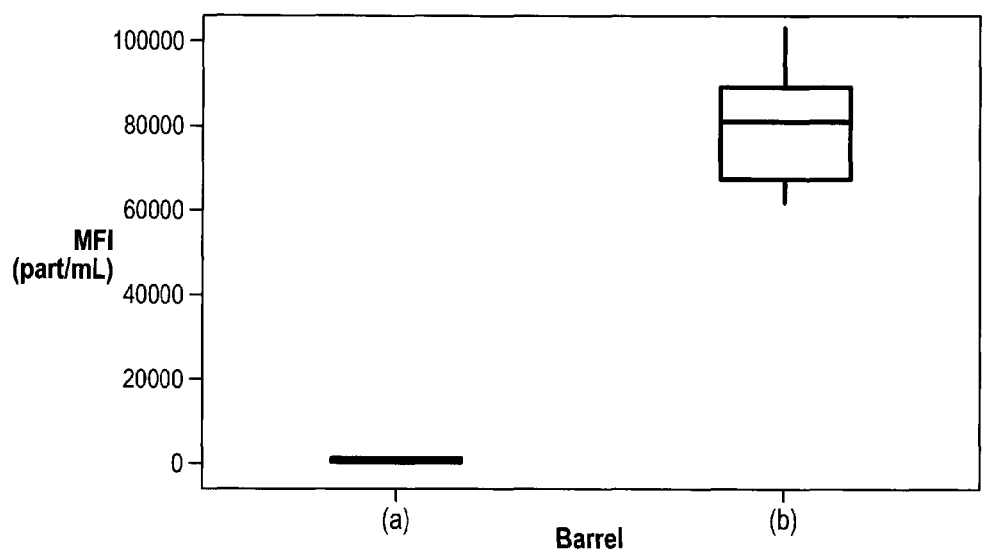
FIG. 7 shows the particle level measured by MFI™ in a syringe containing a lubricant coating according to the invention (a) and a syringe containing a PDMS layer (b)

FIG. 7 shows the particle level measured by flow microscopy in 1 ml long syringes coated with a lubricant coating according to an embodiment of the invention, obtained by the above-defined "1 ml long plasma treatment" (value (a)) and in 1 ml long syringes siliconized with PDMS (value (b)).

This value (b), obtained for a PDMS layer, was around 80000 particles/ml.

In comparison, the value (a) obtained for the lubricant coating 5 was below 4800 particles/ml which is more than 14 times less.

In other words, the particle level generated by a lubricant coating 5 according to the present invention represents around 6% of the particle level generated by a PDMS coating, when measured by MFI™.

Figure 8:
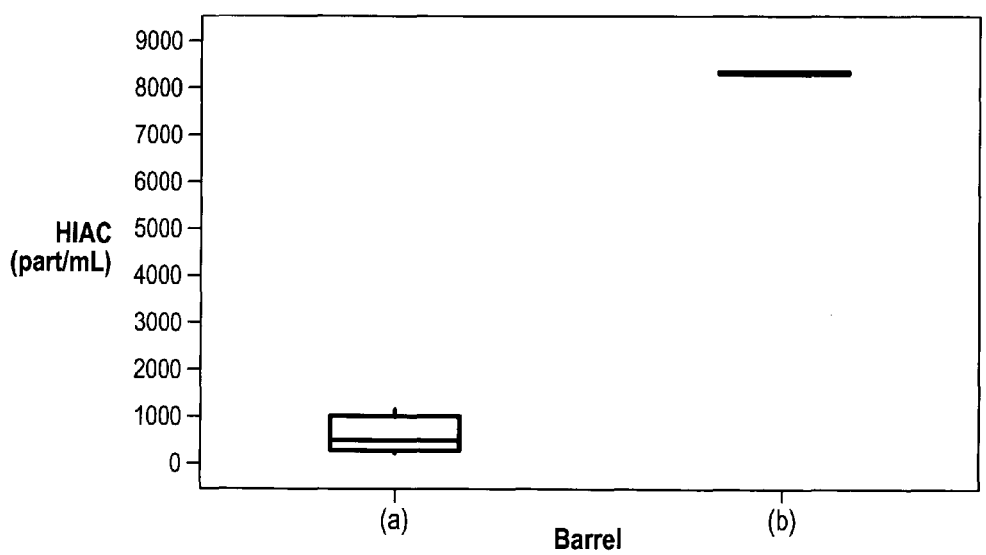
FIG. 8 shows the particle level measured by HIAC in a syringe containing a lubricant coating according to the invention (a) and a syringe containing a PDMS layer (b)

Similarly, FIG. 8 shows the particle level measured by HIAC in a 1 ml long glass syringe coated with a lubricant coating 5 obtained by the above-defined "1 ml long plasma treatment" (value (a)) according to an embodiment of the invention and in a syringe coated with PDMS (value (b)).

The average particle level of a coating according to the invention is of 1500 particles/ml (value (a)) and thus very low in comparison to the 8500 particles/ml obtained from a PDMS coating, more precisely around 71 times less.

In other words, the particle level generated by a lubricant coating 5 according to the present invention represents around 17% of the particle level generated by a PDMS coating when measured by HIAC.

As particles are generated by the surface of a coating, particle values can be expressed by number per surface unit, i.e. particles per $mm^2$. In this case, the particle level generated by a lubricant coating 5 is less than 2.11 particles per $mm^2$ of coating when measured by HIAC Light Obscuration method and less than 10.56 particles per $mm^2$ of coating when measured by flow microscopy.

The difference between the particle level measured by HIAC and by MFI™ is explained by the different sizes of particles measured by the two apparatus: the HIAC apparatus measures particle sizes ranging from 2 to 400 μm while the MFI™ measures particle sizes ranging from 1 to 100 μm. Moreover, small sized particles are generated in higher quantities by a PDMS coating, while big sized particles are generated in smaller amount.

As a result, the reduction of the particle level provided by a lubricant coating 5 versus a PDMS coating is more significant when smaller sized particles are considered, than with the MFI™ technique.

To conclude, this coating shows both with HIAC and MFI™ a very high improvement in terms of particle level in comparison to a PDMS coating. This allows the reduction of toxicity for patients while substantially gives an increase in the stability for high value drugs stored in a medical container. Indeed, a lubricant coating emitting a low level of particles in the stored pharmaceutical composition prevents denaturation and degradation of this composition.

Gliding Force of the Stopper within the Barrel

In order to evaluate the gliding force of a stopper into a lubricated barrel, an empty 1 ml long glass syringe closed by a Daikyo Flurotec® stopper was connected to a traction-compression bench (Lloyd LRX Plus) for inducing the gliding of the stopper within the container.

The bench was used for compression at a speed of 380 mm/min with no preload and the reference used was similar syringes lubricated with a PDMS coating with similar thickness.

FIG. 9 shows the gliding force of the stopper within a barrel lubricated with the lubricant coating according to an embodiment of the invention, obtained by the above-defined "1 ml long plasma treatment" (a) and a barrel lubricated with a PDMS coating (b).

This graph shows that the gliding force of a stopper in a syringe barrel comprising the lubricant coating is around 3 N higher than the gliding force of a stopper in a syringe barrel having a PDMS coating.

However, the average gliding force remains around 5 N and below 8 N, which is a suitable range for syringe applications.

More precisely, the gliding force obtained with syringes lubricated with a lubricant coating 5 was in the range of 3 to 6 N.

Thus, a lubricant coating 5 according to the present invention provides a low particle level into the pharmaceutical composition, a very good compatibility with vaccines and biotech drugs and good mechanical properties, while preserving an acceptable gliding force.

Then, in order to estimate the behavior of the coating over time, measurement of the gliding forces was performed on 1 ml long syringes lubricated with a lubricant coating according to the present invention, obtained by the above-defined "1 ml long plasma treatment", directly after manufacturing, and after 1 month of storage under 40° C. and 75% of relative humidity.

In parallel, a visual check was performed to ensure that no delaminating or break-up occurred during the one month period.

The result of this experiment can be shown on FIG. 10 where the gliding force after a 1-month storage "T1" (on the left) is essentially similar to the gliding force measured without a storage period "T0" (on the right).

It can thus be concluded, from this experiment, that the lubricant coating specific composition enables to maintain its advantages over time which is particularly interesting in the field of prefilled medical containers.

Indeed, as prefilled medical containers are stored in pharmacy, warehouse or hospitals for a period ranging from 12 to 24 months or more before being used by medical staff, a lubricant coating according to the present invention ensures a constant level of gliding whatever the storage period.

Finally, it should be noted that the lubricant coating shows a low risk of unpredictable side effects as it is based on classic PDMS silicone oil which has been submitted to extensive toxicology tests and is currently authorized for medical use.

While specific embodiments of the invention are described with reference to the figures, those skilled in the art may make modifications and alterations to such embodiments without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A lubricant coating for a medical device, comprising:
    a bottom layer in contact with a surface of the medical device to be lubricated, comprising a mixture of cross-linked and non-cross-linked poly-(dimethylsiloxane);
    an intermediate layer consisting essentially of oxidized poly-(dimethylsiloxane) and having a thickness between 10 and 30 nm; and
    a top layer consisting essentially of non-cross-linked poly-(dimethylsiloxane) and having a thickness of at most 2 nm.

2. The lubricant coating according to claim 1, wherein the bottom layer is a gel.

3. The lubricant coating according to claim 1, having a thickness between 90 and 400 nm.

4. The lubricant coating according to claim 1, wherein the thickness of the bottom layer is between 58 and 388 nm.

5. The lubricant coating according to claim 1, wherein the formula of the oxidized poly-(dimethylsiloxane) of the intermediate layer is:

$[SiO(CH_3)_{2-x}(OH)_x]_n$, where x ranges from 0.2 to 1.5 and n is an integer.

6. The lubricant coating according to claim 5, wherein x=0.75.

7. The lubricant coating according to claim 5, wherein n ranges from 70 to 100.

8. The lubricant coating according to claim 1, wherein the thickness of the intermediate layer is between 15 and 25 nm.

9. A process for manufacturing a lubricant coating, comprising:
    depositing a layer of poly-(dimethylsiloxane) on a substrate, the thickness of said layer being between 90 and 400 nm; and
    exposing said layer to an oxidizing plasma, so as to form said lubricant coating by oxidizing and cross-linking at least part of the poly-(dimethylsiloxane),
    wherein said oxidizing plasma is carried out in an atmosphere comprising oxygen and argon,
    wherein the atmosphere of said oxidizing plasma contains oxygen and argon with respective partial pressures between 15 and 30% for oxygen and between 70 and 85% for argon, and
    wherein the step of exposing is an exposure between 10 and 40 seconds.

10. The process according to claim 9, wherein a viscosity of the deposited poly-(dimethylsiloxane) is between 900 and 1200 cSt at 25° C.

11. The process according to claim 9, wherein the oxidizing plasma is generated by radio-frequency, with a power ranging from 50 to 300 W, and under a vacuum in the range 1.33-13.3 Pa (10-100 mTorr) in absolute value.

* * * * *

UNITED STATES PATENT AND TRADEMARK OFFICE
CERTIFICATE OF CORRECTION

PATENT NO. : 9,993,597 B2
APPLICATION NO. : 14/404153
DATED : June 12, 2018
INVENTOR(S) : Cédric Foucher et al.

Page 1 of 1

It is certified that error appears in the above-identified patent and that said Letters Patent is hereby corrected as shown below:

On the Title Page

Column 1, Item (73) Assignee, delete "Point" and insert -- Pont --

Signed and Sealed this
Twentieth Day of November, 2018

Andrei Iancu
*Director of the United States Patent and Trademark Office*